United States Patent [19]

Baldwin

[11] Patent Number: 5,084,021

[45] Date of Patent: Jan. 28, 1992

[54] PATIENT CONTROLLED INFUSION APPARATUS AND METHOD

[76] Inventor: Brian E. Baldwin, 7891 S. Argonne, Aurora, Colo. 80016

[21] Appl. No.: 608,283

[22] Filed: Nov. 2, 1990

[51] Int. Cl.$^5$ .............................................. A61M 5/00
[52] U.S. Cl. ..................................... 604/131; 604/236
[58] Field of Search ............... 604/131, 134, 135, 137, 604/138, 207, 236, 246

[56] References Cited

U.S. PATENT DOCUMENTS

| | | | |
|---|---|---|---|
| 4,298,000 | 11/1981 | Thill et al. | 604/135 |
| 4,597,754 | 7/1986 | Thill et al. | 604/135 |
| 4,828,551 | 5/1989 | Gertler et al. | 604/236 |
| 4,857,056 | 8/1989 | Talonn | 604/135 |
| 4,863,429 | 9/1989 | Baldwin | 604/235 |
| 4,904,243 | 2/1990 | Bruera | 604/208 |
| 4,966,585 | 10/1990 | Gangemi | 604/135 |

*Primary Examiner*—Paul J. Hirsch

[57] ABSTRACT

Patient controlled analgesic (PCA) infusion apparatus and method are disclosed, in which a liquid desired to be self-infused into a patient is controllably supplied from a positively pressurized supply reservoir to a lower pressure dose chamber of a patient operable syringe from which the patient may expel the liquid and infuse such into a suitable infusion site, as through a cannula inserted into the patient, the supply of liquid from the reservoir to the dose chamber being controlled by a flow control metering tube assembly, including a connecting tube with a flow-restricting metering rod disposed therein and of a selected effective length such that the combined flow impedance of the flow path formed by the overall flow metering tube and rod provide a selected flow rate for a reference fluid and reference pressure differential. The flow control metering tube assembly may be suitably constructed by empirical testing and sizing of individual flow control tube/rod assemblies to achieve a desired flow impedance. A suction, preferrably forming a vacuum-induced void, is automatically effected in the dose chamber by a return spring acting on a piston forming a rear wall of the dose chamber, after each infusion by the patient, so as to effect a desired selected substantially constant refill flow rate of liquid from the supply reservoir and into the dose chamber. A check valve is provided in an outlet tube to enable patient actuated infusion outflow of liquid from the dose chamber while opposing reverse inflow back into the dose chamber, and thus aiding in enabling a desired suction vacuum induced void to be created within the dose chamber during the dose chamber refill operation as a function of fast rearward spring acting return movement of a piston forming the movable rear wall of the dose chamber.

35 Claims, 5 Drawing Sheets

PATIENT CONTROLLED INFUSION APPARATUS AND METHOD

This invention relates to an apparatus and method for patient controlled infusion of an analgesic or other desired liquid medicament into a patient, and more particularly to such apparatus and method in which flow rate re-supply of infusion liquid to a dose chamber, from which the medicament may be expelled by the patient, is closely controlled so as to accordingly closely control the maximum total volume of liquid medicament that a patient may self-infuse over a given period of time.

Numerous devices are currently used for patients to administer their own pain control medication or other patient controlled infusion of injectable medications. The systems currently in use are predominantly electronic devices. One non-electronic elastomeric infusor is in use, the Baxter Half Day Infusor and PC Module which are used in tandem. This device and 15 electronic controlled devices are shown in the 5th Annual Buyers Guide to Pumps & Controllers published in Pharmacy Practice News, July 1989.

Numerous publications have reported on patient controlled analgesic (PCA) through patient controlled infusion of an analgesic liquid. Among these publications are "The Tragedy of Needless Pain", Melzack, February, 1990 Scientific American; "Parenteral Analgesics in the Terminal Patient", Patton et al, March 1990, U.S. Pharmacist; "High-Technology IV Infusion Devices", Kwan, February 1989, American Journal of Hospital Pharmacy; and "Hospital Pharmacy-Based Service for Patient-Controlled Analgesia", Wong, et al, February, 1990, American Journal of Hospital Pharmacy.

In the February, 1990 Scientific American publication, one reference cited is "Influence of the Pain and Symptom Control Team (PSCT) on the Pattern of Treatment of Pain and Other Symptoms in a Cancer Center", Bruera, et al, Journal of Pain & Symptom Management, September, 1989. U.S. Pat. No. 4,904,243 was issued to the author, Bruera, and discloses a syringe with a one way check valve and a plunger which is manually manipulated for withdrawing solution from a source container. The device is to be used to self administer the contents of the syringe. The device of Bruera U.S. Pat. No. 4,904,243 is simple and has no spring return, and the patient is to provide fill suction action on the syringe plunger, thus leaving this important refilling aspect to wide variations in refill rate, dependent on the patient's actions.

Gerlter U.S. Pat. No. 4,828,551 shows another all mechanical syringe infusor for PCA with a spring return of the injection syringe for aspirating the medication from a reservoir with flow rate regulated by the spring force, flow path restriction and viscosity of the solution.

A commercially available PCA apparatus marketed by Baxter Healthcare Corporation and identified as Baxter (Travenol) PCA Infusor, is a wrist watch type module with a chamber filled from a pressurized elastomeric reservoir. A publication dated September, 1988 entitled "Travenol Infusor Preparation Guide", describes this device.

Numerous various spring return syringe devices with one way check valves used for transfer of fluids are available.

To provide an effective usable PCA, the system should have the dose volume be substantially accurate since a typically employed volume is 0.5 cc and a 0.1 cc variation is an unacceptable 20% error. The chamber should refill in a defined constant time period and be filled at a substantially constant rate. If a refill time is 6 minutes, and the patient were to inject every one minute, the amount injected each minute needs to be not more than one-sixth of the 0.5 cc.

With a spring return infusion syringe there are problems with obtaining a constant rate of flow since the suction pressure is greater at the beginning and will decrease at a linear rate as the syringe piston moves to the filled position.

In the Baxter (Travenol) PCA Infusor, an elastomeric bladder chamber of a wrist watch container is filled from a pressure source through a flow control connecting tube. The patient actuates the dose by pressing a button on the watch container which depresses a spring to open a pinch clamp on an outlet tube, and with further motion it presses the fluid out of the bladder chamber containing 0.5 cc of fluid. There have been problems with this device in actual use, where the spring either broke or the button stuck in the depressed position. This caused the patient to receive a continuous dose of drug. It is clear that this is not a fail safe device.

Various means of control of liquid medication flow rate from one site to another have been in commercial use where the fluid source is at a substantially constant pressure. Substantially constant pressure has been achieved by various means including constant height, constant spring force on a syringe piston, constant gas pressure on a syringe piston, and inflated elastomeric fluid containers.

Flow regulation has been achieved through use of a glass capillary as in Thill U.S. Pat. No. 4,298,000 which employs a capillary tube flow restrictor within a larger flow tube controlled by liquid passage through the capillary tube bore, and in Baldwin U.S. Pat. No. 4,863,429, in which lengths of tubing of selected length and ID are employed. The Baldwin patent describes use of an assortment of tube sets with defined flow rates when used with a known pressure on a reference fluid source, and further describes flow rate adjustment by change of the length and/or internal diameter of the flow control tubes.

This prior art required very high precision of the ID of the small diameter flow control tube or the capillary tube, since flow rate is proportional to the fourth power of the flow tube inside diameter, and the smaller the required internal diameter the more difficult it is to acceptably control the tolerance of the ID. The Baldwin prior art describes the final adjustment by change of the length. At the present state of commercial production tolerances, this has been found to result in tube lengths inconvenient for the intended use. In addition the small ID needed to achieve the low flow rates and the OD needed to provide adequate tube tensile strength are found to require double extrusion. The heavy wall of the tube was found to cause the ID size control to be very difficult to achieve in commercial practice.

An object and feature of the invention is to provide an acceptably reliable substantially fail safe device for patient self injection or infusion of medication.

A further object is to provide a low cost PCA apparatus and method.

Still a further object and feature of the invention is to provide a PCA infusor and method which enable substantially constant flow rate repeated refilling of a fixed dose volume chamber of the infusor, using a simple spring return syringe element.

A still further object and feature is to provide an apparatus and method in which a patient is enabled to self administer a substantially precise maximum total volume of the medication, and in which a substantially constant medication refill rate is achieved irrespective of the frequency of actuation and self-administered injection by a patient.

Still other objects, features and attendant advantages will become apparent to those skilled in the art from a reading of the following detailed description of an illustrative and preferred embodiment of the invention, taken in conjunction with the accompanying drawings, wherein FIG. 1 generally illustrates a patient controlled liquid medication infusion apparatus according to the invention.

Figure 1:
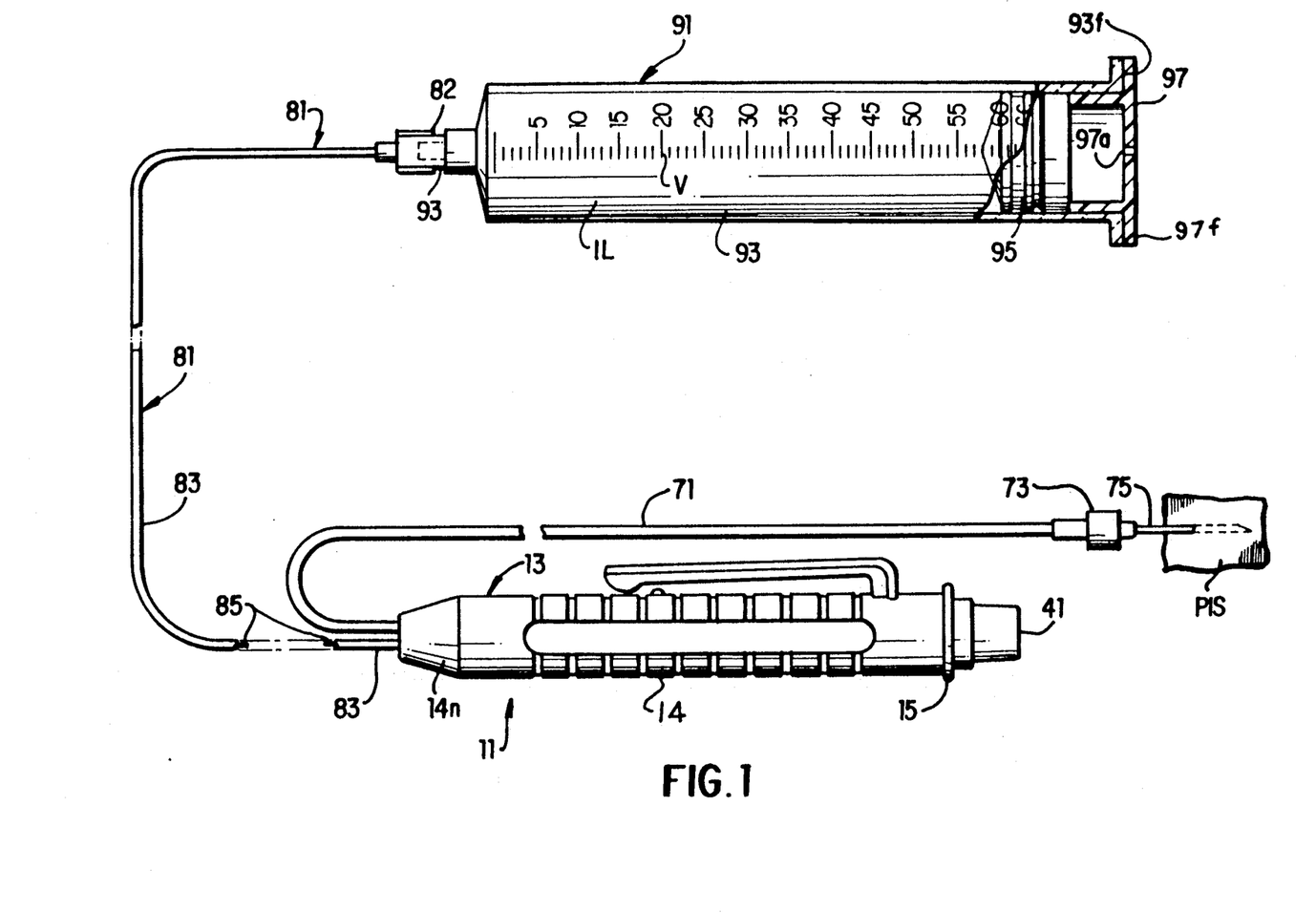
Figure 2:
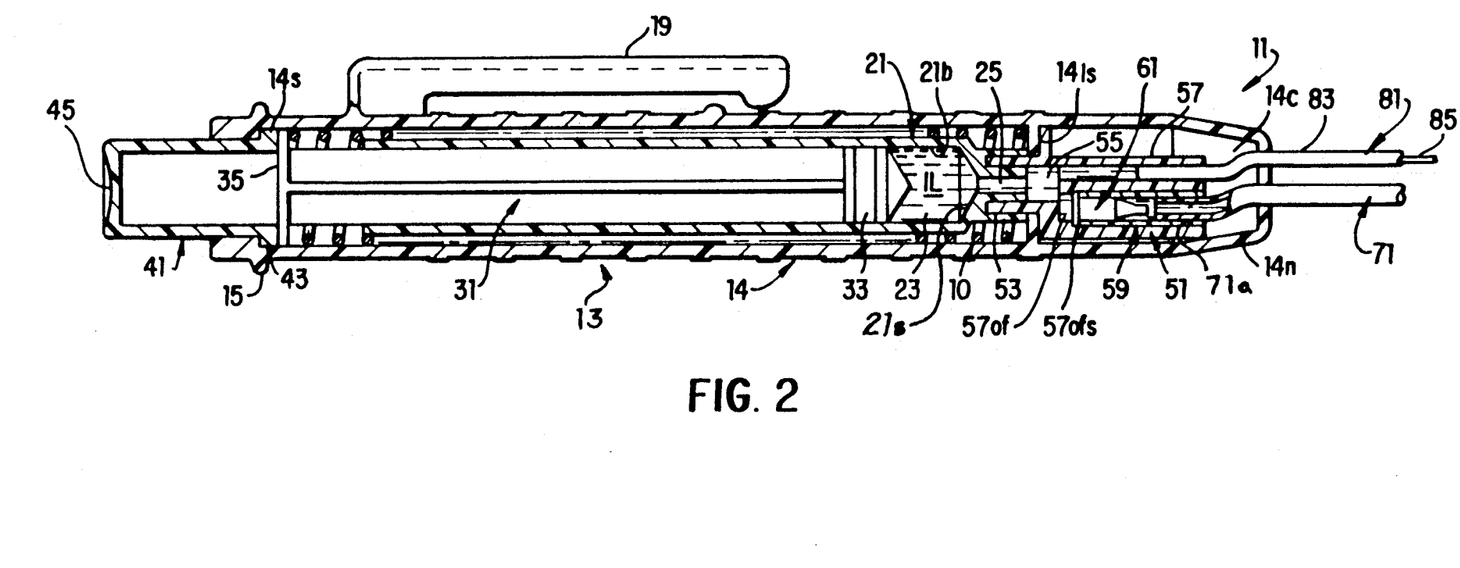
FIG. 2 is a longitudinal section view of the patient actuated infusion syringe or infusor of FIG. 1, showing the syringe dose chamber filled with liquid and ready for patient actuated infusion operation.

Referring now in detail to the Figures of the drawings, patient controllable analgesic (PCA) infusion apparatus 11 is provided, including an automatically refillable patient controllable infusion syringe or infusor 13, the major parts of which may be formed of plastic or other desired material although the spring 10 is preferably conventionally formed of metal and the piston 33 is preferably formed of rubber, as is conventional practice. Refill of infusor 13 is automatic and is metered through a flow control metering tube assembly 81 connecting a dose chamber 23 of the infusor 13 to an infusion liquid medicament IL supply reservoir, which in the illustrated and preferred embodiment takes the form of a syringe 91. The infusor 13 has a depressible push button 41 which preferably may easily be pressed forward by a patient while grasping the infusor 13 and applying finger pressure to the concave end surface 45 of push button 41 to move a plunger 31 and fluid-sealing piston 33 forward within a syringe barrel 21 to expel a dose of desired infusion liquid medicament IL from a dose chamber 23 therein to an infusion site PIS through a check valve 61 and suitable outlet or outflow tube 71 and a cannula or other desired infusion site applicator 75, which may be suitably removably connected to the end of outflow tube 71 as by a conventional Luer connector 73.

Liquid supply reservoir syringe 91 includes a barrel 93, which may suitably have volumetric indicia V visibly formed therealong for ease of generally checking on the quantity of liquid medicament used by the patient over a period of time. Reservoir syringe 91 has a follower piston 95 which is open to atmospheric pressure through a vent opening 97a in a protective end cap 97 which is provided to prevent the piston 95 from being pushed other than by normal differential pressure acting movement thereof by normal operation of the system. Cap 97 is suitably seated in place as by seated engagement between cap flange 97f and the flange 93f on the open end of barrel 93.

It is desirable that the friction between reservoir syringe 91 and piston 95 be as low and uniform as feasible in order to minimize friction losses and variations resulting from this movement interface zone, so as to enable maximizing of the advantages of the invention, an important advantage and feature of which lies in aiding in effecting a substantially constant liquid refill rate from supply reservoir 91 to dose chamber 23 of infusor 13.

Infusor 13 includes a case 14 which may be suitably molded of two suitably secured together longitudinal halves, and having a tapered nose end 14n through which inlet/outlet tubes 71, 81 extend, and a hollow cavity 14c which is open at its rear end and which houses a syringe barrel 21 open at its rear end to accommodate assembly and longitudinal movement of a plunger 31 and liquid sealing piston 33 therewithin.

Syringe barrel 21 is suitable securely mounted within case 14 at its reduced diameter nose end 21n by securing engagement with the rear section 53f of an assembly connector 51, the secured engagement therebetween thereby fixing the barrel 21 snugly against one end face of annular internal lip shoulder 141s of case 14, while fixing the connector 51 in secured position extending through and snugly against the opposite wall of the annular lip shoulder 141s. This interfitting securement of barrel 21 and connector 51 may be suitably effected as with a press fit and suitable adhesive, or otherwise as may be desired, to achieve a suitably reliably sturdy construction.

Inlet or inflow tube 83 of flow control metering tube assembly 81 is suitably anchored as at 81a within an inflow or inlet bore 57 if formed in the forward section 57 of connector 51. Entrance end 71a of outflow or outlet tube 71 is anchored within outflow or outlet connector bore 57 of through the medium of a resilient plastic sleeve 59 which also conveniently serves as a mount for and locates a suitable check valve 61, such as a duck bill valve, which permits ready outflow of liquid while opposing reverse or inflow of liquid. Sleeve 59 enables employment of a lesser diameter outlet tube 71 than the diameter of bore 57 of which may be required to accommodate a given particular check valve, such as duck bill check valve 61. A suitably larger OD outlet tube 71 may be suitably directly secured within bore 57 of if desired, in which event check valve 61 may be suitably secured within one end of the tube 71, or otherwise suitably mounted, instead of through the intermediate securing sleeve 61 of the illustrative embodiment.

Inlet and outlet tubes 71 and 83 and sleeve 61 may be suitably fixedly secured within connector 51, as by welding with plastic adhesive or by other desired means, as may be desired.

Connector 51 has a central common bore 55 connecting between each of inlet bore 57 if and outlet bore 57 of and an inlet/outlet bore 25 formed in the nose end 21n of syringe barrel 21, and which in turn forms the passageway for fill/refill inflow of liquid medicament into dose chamber 23 and liquid medicament outflow from dose chamber 23 during infusion of a desired liquid medicament.

Dose chamber 23 is formed at the forward end of barrel 21 and is bounded by the cylindrical side wall 21b of syringe 21, the tapered forward face of piston 33 and correspondingly complementarily tapered end seat 21s formed at the forward end of barrel 21. The maximum total volume of dose chamber 23 is fixed by limiting the rearward travel of piston 33, as through the medium of case annular shoulder stop 14s which is engaged by push button flange 43 to stop further rearward movement of the push button 41, as well as piston 33 and ribbed plunger 31 connected thereto, the flanged rear end 35 of which plunger 33 engages with push button 41 and is resiliently pushed thereagainst by a piston return compression spring 10 within case 14 and surrounding barrel 21.

Case 14 may be suitably formed of plastic and may desirably have a pocket clip 19 formed thereon, which enables removable securing of the infusor 13 to a patient's clothing or to the bed linen or otherwise as may be desired.

Case 14 may suitably have an external annular flange 15 formed at its rear end adjacent push button 41 for ease of holding the infusor 13 during manual depressing of the push button 41.

Flow control metering tube assembly 81 takes the form of a flexible plastic tube 83 having a fluid transmission bore 84, within which is disposed a flexible flow restrictor rod 85, which is a solid rod or has other suitable construction which forms an effective fluid flow blocking cross-section to fluid flowing within tube bore 84. Flow restrictor rod 85 has an outer diameter less than the ID of bore 84 such as to permit liquid flow therearound, while effectively reducing the flow passageway cross-sectional area along the length of rod 84. This arrangement and method affords a powerful and facile way for providing a flow control tube assembly having a selected flow control rate.

Figure 3:
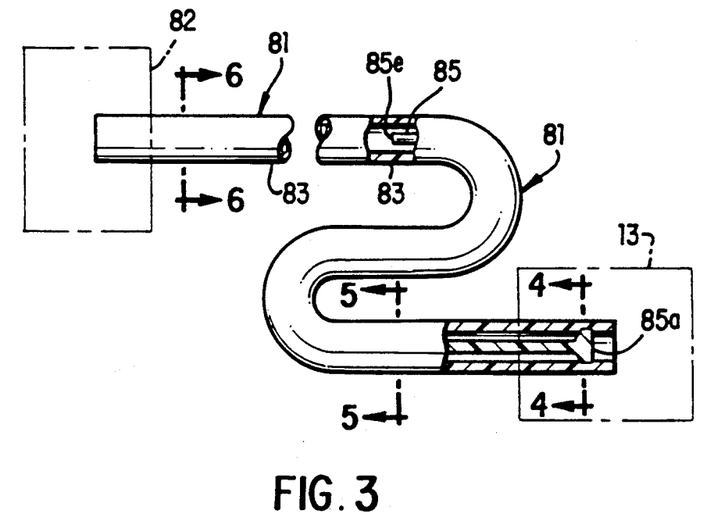
FIG. 3 illustrates the flow metering connector tube assembly of FIG. 1 as employed in a presently preferred embodiment of the invention.
Figure 4:
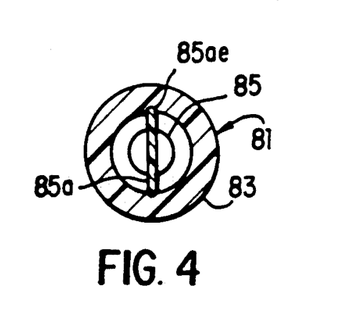
FIGS. 4-6 are section views of the metering connector tube assembly taken on lines 4—4, 5—5 and 6—6 of FIG. 3.
Figure 5:
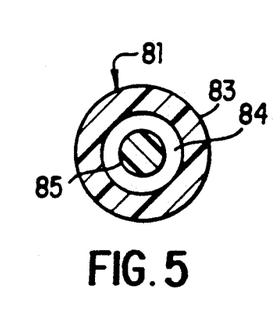
Figure 6:
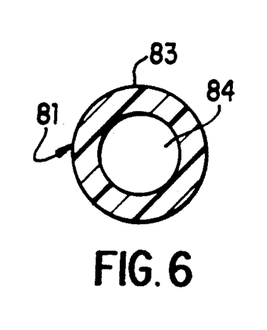

Flow restrictor rod 85 may be suitably anchored at one end of the tube 83, at either the entrance or exit end, as by physically pinching a short end segment 85 thereof to a flattened and widened cross section 85a, the opposite outer edges 85ae of which are slightly larger than the inner diameter of tube bore 84, so as to slightly resiliently deform the bore inner wall surface when the pinch-deformed segment 85a is pushed into the end of tube 83, thereby effectively frictionally anchoring the tube and rod 85 together.

Other suitable means may also be employed for longitudinally retaining the rod 85 in place. For instance, it has been found that the rod will be longitudinally generally self-retained in place when the rod length exceeds 300 diameters of the rod 85.

Flexible flow restrictor rod 85 may be suitably formed of flexible (yet sufficiently stiff to resist longitudinal collapse under flow pressure) plastic material such as polycarbonate, polysulfone, or other suitable material as desired, being sufficiently flexible to flex from side to side with and within tube bore 84, the OD of rod 84 being normally very small (e.g. typically approximately 0.008–0.014 inch or the like) in practice in view of the small tube diameter sizes normally found to be desirably employed in medical liquid infusion devices. The combination of the small lateral clearance (e.g. approximately 0.003–0.04 inch) between the tube bore wall and the outer annular surface of rod 85 together with the inherent stiffness of the rod 85 serve to prevent collapse of the rod along the bore 84 when employing a rod anchored at the exit end of tube 83.

Rod 85 may be sized as desired both in length and diameter to achieve a desired flow rate for a given reference fluid and pressure differential between the opposite ends of flow control metering tube assembly 81.

Flow control metering tube assembly 81 is more particularly described in my copending patent application entitled Flow Metered Tube Arrangement and Method, Serial Number 608381, to which reference is made and which is incorporated herein by reference for further more specific details of construction, mode of operation and features.

By suitably choosing the diameter of tube bore 84 and the diameter of flexible rod 85, a suitable reduced flow passageway of reduced cross-section may be formed along the length of rod 85 such that for a given desired range of flow rates an assortment of flow control tube assemblies may be provided, each with a combined tube length and bore diameter, rod length and diameter that together provide a selected flow rate for a given reference fluid and flow pressure differential. While it is possible to theoretically calculate a fluid flow rate through a given sized flow control tube assembly 81, it has been found in practice that due to various manufacturing tolerances and the variables, for desired practical precision manufacture of tube assembly 81 it is desirable to test each tube assembly individually with a reference fluid and pressure differential, making adjustment of the rod length to achieve a desired flow rate, after which rod 85 is cut to the empirical test determined length and pinch deformed to a flattened wider configuration as shown at 85a and pushed into the tube 83 to anchor the rod within the tube bore 84.

By selecting a suitably convenient overall tube length and bore ID, conveniently useable lengths of flow control tube assemblies 81 may be provided for the infusion apparatus and method, through employment of various OD's and lengths of rod 85, in combination with the selected convenient tube length and a given selected bore ID for providing a given selected flow rate, as may be determined from individual empirical testing and adjustment of rod length.

Figure 8:
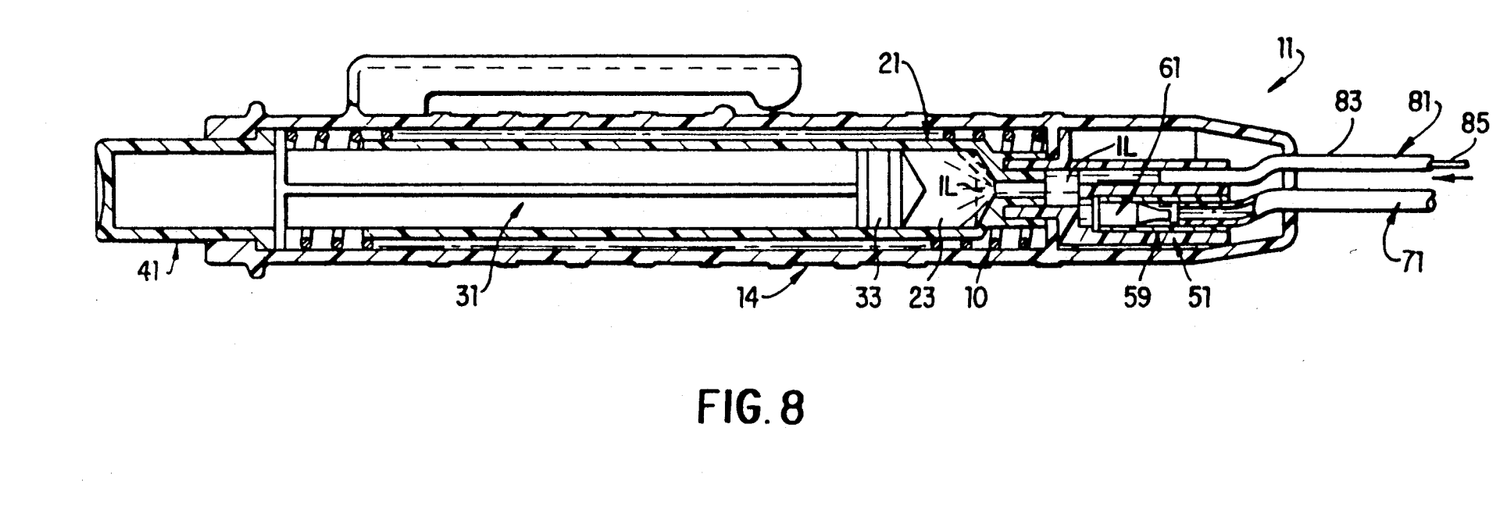
FIG. 8 is a view similar to FIG. 7, illustrating the syringe after release of the manual push button and return of the syringe piston to its rearmost position, and showing the formation of a vacuum or suction induced void within the dose chamber and illustrating flow of liquid into the void from the liquid supply reservoir and through the flow control metering tube assembly.

A patient controllable infusion apparatus 11 is thus provided, including a refillable or rechargeable infusion syringe or infusor 13 having a syringe barrel 21 and fluid sealing expulsion and suction piston 31 as major components to produce both a positive infusion-effecting pressure and a suction- or vacuum-induced substantially constant fill/refill or charge/recharge pressure within the syringe dose chamber. This suction pressure is effected by a spring 10 return force acting on the piston rod 35 upon release of push button 41 after manual forward movement and release of push button 41 and piston 33. The force of the spring 10 should be sufficient to reliably and quickly overcome the friction of the piston 33 sliding within the syringe barrel 21 and to effect rearward movement of the piston 33 at a rate such as to form a vacuum induced void within the dose chamber 23, such that the piston 33 separates from any liquid within the dose chamber formed within barrel 21 forward of the piston or within the supply passageway to the dose chamber, as a function of rearward movement of the piston 33 to its rearmost position. The resulting vacuum pressure within this vacuum induced void is substantially constant due to the vaporization of the residual infusion liquid in the dose chamber zone reaching an equilibrium vapor pressure, with subsequent condensation during refill of the dose chamber 23 maintaining the substantially constant equilibrium vapor pressure under conditions of substantially constant temperature. Small variations, less than 8%, in the pressure of the vacuum induced void have been measured, believed to be due to dissolved gas in the infusion liquid. This small deviation from constant pressure has not been found to have a significant effect on refill rate linearity, and accordingly the term "substantially constant pressure" as used herein is intended to encompass this small inherent pressure variation, which has been found to be of substantially no significant effect on the refill rate of the infusor liquid into the dose chamber 23.

By effecting this vacuum-induced void in the dose chamber the total dose chamber 23 will refill with liquid under a constant negative suction pressure relative to atmospheric pressure. If a lower spring 10 force is used, such that the piston 33 does not separate from the liquid, the suction pressure within the dose chamber 23 will be a function of the spring force and the friction force of the piston with respect to employment of a vacuum induced void for aiding in obtaining a substantially constant dose chamber refill rate, while health care personnel may have briefly pulled a vacuum induced void in filling syringe through the outlet cannula there, such is only a brief and unsustained essentially inadvertent action, and is not for purposes of achieving a substantially constant refill rate, and to my knowledge a vacuum induced void has not been employed in a refillable dose chamber of a patient-controllable infusion arrangement and method for effecting a substantially constant liquid medicament refill rate. Likewise, while evacuated blood collecting containers have been commonly employed for several years, such are provided or employed for controlling the rate of liquid flow into the containers, such evacuated containers being simply single use collection devices which replace the conventional manual suction syringe in sample collecting.

Referring further to the dose chamber piston/barrel wall interface, tests of piston/barrel arrangements have indicated that the friction force between the piston and barrel is difficult to control, due to variations of dimensions of the rubber and plastic parts, as well as the lubrication of the piston-barrel interface. In addition, the coil spring 10 produces a force which will vary with its degree of compression and thus with the movement and linear position of the plunger 31 and piston 33. With a lower spring 10 force below that which is necessary to effect a vacuum-induced dose chamber void, the system would also encounter deviations in flow rate related to the variations of the spring rate and spring forces due to manufacturing tolerances of springs.

The employment of a larger spring force moves the piston 33 quickly and substantially immediately back to the end of its travel where the plunger 31 is stopped by the end flange 35 of the plunger 31 and the shoulder flange 43 of push button 41 reaching the limit of rearward travel by engagement of shoulder flange 43 with shoulder stop 14s of the case 14. By providing a spring biased piston 33 return rate of travel rearwardly such that the dose chamber volume is increased at a rate faster than the liquid refill flow rate into the dose chamber, a suction or vacuum-induced void is formed having a substantially constant internal suction pressure. This allows a dose chamber volume of e.g. 0.5 Ml effected by the piston 33 rearward movement displacement to be filled with a substantially constant suction pressure, which is negative relative to atmospheric pressure acting on supply reservoir piston 95, throughout the filling time. The many variables of spring 10 force, and infusor piston 33 friction may thus be effectively eliminated by employment of this aspect of the invention.

Refill of the dose chamber 23 after rearward piston displacement is effected through flow control tube assembly 81. As previously indicated, however, the preferred construction and method of construction of the flow control tube assembly 81 is to form a fixed length (e.g. 36 inch) tube 83, of e.g. approximately 0.010 to 0.016 inch bore inside diameter, with an empirical test-determined selected length and diameter of rod extending along a length of the tube bore 84, which rod 85 may typically and suitably have an outside diameter in the range of 0.008 to 0.014 inch for providing a desired flow restriction-forming flow impedance.

In use, a patient is given the infusion apparatus 11 with a prefilled fixed dose volume of e.g. 0.5 Ml, the apparatus being preconstructed to provide a fixed refill flow rate, usually 6, 10 or 15 minutes to refill the 0.5 Ml volume If the patient should press the button 41 in less than the refill time, the dose received will thus be proportionately less. If the button is pressed after 3 minutes while using a device set for a 6 minute refill time, the dose injected will be 0.25 Ml.

Figure 7:
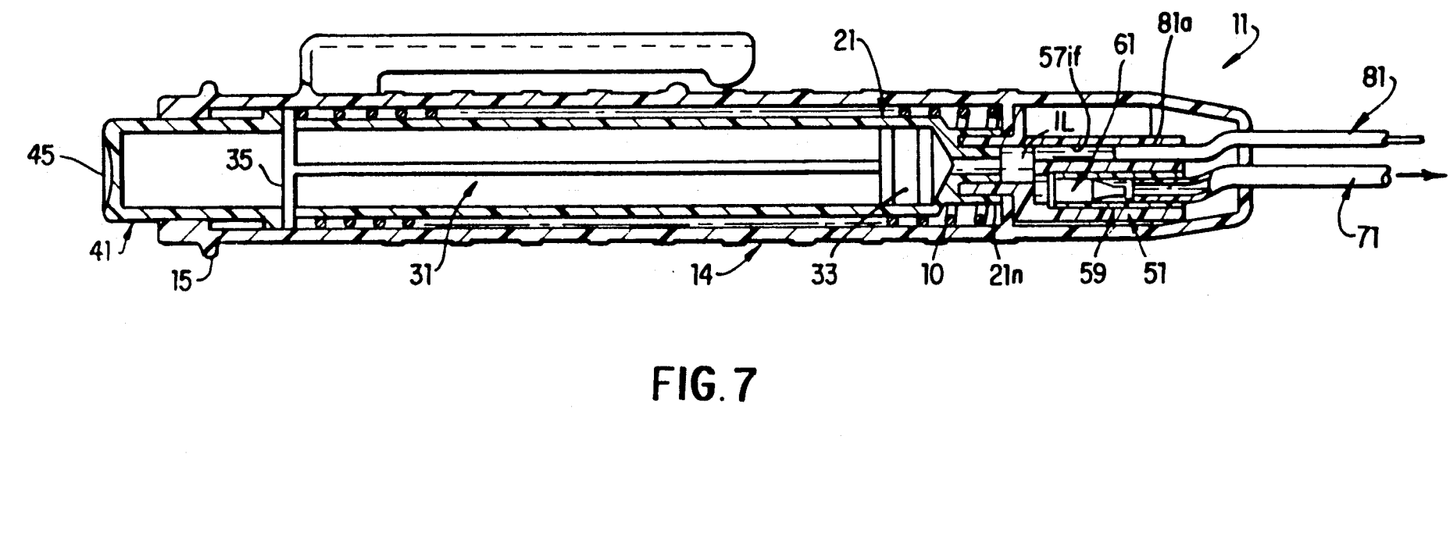
FIG. 7 is a view similar to FIG. 2, showing the syringe at completion of infusion through expulsion of liquid from the dose chamber, with the manually actuatable piston moved fully forward and ready to be released for initiating refill of the dose chamber.

When the push button 41 is pressed, the dose liquid within dose chamber 23 passes out through the one way duck bill check valve 61 and outlet tube 71. As the push button is released, the spring 10 returns the piston 33 to its rearmost stopped position as shown in FIG. 8, creating desired negative suction pressure relative to atmospheric pressure, and by movement of piston 33 at a rate such as to enlarge the dose chamber volume faster than the rate of liquid refill flow through tube assembly 81, a desired automatic-suction- or vacuum-induced void will be formed within dose chamber 23, with a resultant substantially constant dose negative pressure relative to atmospheric pressure acting on supply reservoir piston 95. Check valve 61 prevents return of liquid from the outlet tube 71 which is connected to the patient infusion site PIS. When the push button 41 is depressed, there is an insignificant amount of liquid flowing back toward the reservoir 91 through the inlet flow control tube assembly 81, as the flow impedance formed by flow control tube assembly 81 is great relative to the flow impedance of the outlet tube 71, and therefore no second one way check valve is required in the inlet line, although such may be so employed if desired.

As previously described, connector 51 is attached to the nose end 21n of the syringe barrel 21 by a press fit connection which deforms the syringe nose end or tip 21n and engages the syringe barrel 21 so that there is a fixed dimensional or spatial relationship between the connector 51 and the syringe barrel 21. This fixed spacial relationship accommodates and secures the syringe barrel 21 and connects 51 to the annular internal lip shoulder 141s of the two case 14 halves and retains the syringe barrel in a fixed relationship to the case 14.

The assembled and secured together two longitudinal case 14 halves control the locations of the injection button 41 which is a free fit in the end of the case 14, the return spring 10 and syringe barrel 21, and the connector 51 with tubes 71, 81 therein. The case has a clip 19 thereon which may be used to attach the infusor or injector to a clothing pocket, or bed linens.

There is an additional variable in producing a constant flow rate. This is the positive pressure on the source reservoir liquid. If the source reservoir is very flexible, such as a bag made of a flexible plastic film, the pressure on the fluid is equal to atmospheric pressure. If the liquid source reservoir is a syringe 91 with a piston 95, as illustrated, then the resulting pressure on the source liquid produced by atmospheric pressure is somewhat less resulting from the pressure drop across the piston 95 due to the friction of the rubber piston 95 moving within the syringe barrel 93.

In use of the PCA infusion apparatus, it is desireable to have the source container protected from being put under pressure by the container being squeezed or pressed so that the internal pressure is increased. If a syringe is used, it is appropriate to have a cap 97 over the open end to prevent the piston 95 within from being pushed. This cap is vented, as at 97a, so that atmospheric pressure is maintained on the liquid medicament protective follower piston 95.

If a flexible plastic bag is used as a liquid source container, the bag should be housed inside of a rigid container so that the bag cannot be squeezed. The liquid source container might be formed by a rolling diaphragm seal within a rigid cylindrical case, while another liquid source container might have a rigid case with a flexible membrane within, which separates the medicament from another fluid which is itself open to atmospheric pressure through a tube which has a hydrophobic filter at the end of the tube which allows passage of air but does not allow passage of the fluid.

With any of the liquid reservoir container arrangements, it is desirable for the medical staff to be able to monitor the amount of drug which is used over a known time period, as by viewing liquid or a liquid-moved indicator in conjunction with volumetric indicia V on the liquid source container.

By way of illustrating a typical illustrative example of practice of the invention, in one typical particular operating embodiment, the infusor 13 has a dose chamber 23 having a diameter of 0.3494 inches with a maximum chamber volume of 0.5 Mls. The wall length of the dose chamber at maximum size, when piston 33 and plunger 31 are moved fully rearwardly, is 0.33 inches, thus providing a push button 41 travel of 0.33 inches for self-infusion by a patient. The cylindrical cross-sectional area of dose chamber 23 is 0.0959 inches, which is thus the effective sealed cross-sectional area of piston 33, which is formed of rubber, or other suitably elastic material, therewithin.

A suitable infusor return spring 10 has a free length of 5.64 inches and a spring rate of 0.83 lbs/in. Spring 10 is compressed to 3.325 inches when assembled and the dose push button 41 is in its rearmost position. The spring force acting when the dose button 41 and piston 33 are in the rearmost position is 1.917 pounds or 870 grams. When the push button 41 is manually fully depressed and piston 33 is moved to its forwardmost position, the push button 41, plunger 31 and piston 33 travel 0.33 inches or 0.84 cm, thereby completing a patient infusion of liquid from the dose chamber 23 to the patient infusion site PIS.

The force of coil compression spring 10 increases by $0.33 \times 0.83 \times 0.27$ pounds during the total forward travel of the piston 33, bringing the total return spring force to 2.19 pounds resiliently acting rearwardly on plunger 41, piston 33 and push button 41, to effect the desired quick and effective almost immediate return of piston 33 to its rearmost position, when released, so as to effect the desired vacuum-induced void within dose chamber 13.

Tests have indicated that with water as a reference test liquid, the absolute pressure within the dose chamber 23 when this vacuum induced-void is formed is substantially constant in a given instance and lies in the range of 0.9 to 1.0 PSI absolute.

With normal atmospheric pressure being a maximum of 15 PSI, the net maximum forward acting pressure on the piston 33 is approximately 14 PSI. The maximum forward net force of the atmosphere acting on the piston 33 is therefore approximately $14 \text{ PSI} \times 0.0959$ inch or 1.34 pounds.

The employment of a spring force of 1.917 pounds at the rear stopped position of the push button 41 has been found to provide an adequate force over the 1.34 pounds force action on the dose chamber piston 33 by the atmosphere (i.e. approximately 0.57 pounds) to overcome the friction of the piston 33 and any friction of the push button 41 in sliding engagement with the case 14.

In this illustrative embodiment in which water forms a reference dose liquid, the flow control tube 81 has an inside diameter of 0.014 inches and a length of 36 inches. The rod diameter to achieve a desired rate of 5 Ml/Hr to produce a nominal refill time of 6 minutes is 0.0115 inch and the length of rod 85 is approximately 11 inches in a given empirically determined instance, but will vary considerably in actual empirically determined practice, due to the manufacturing tolerances normally found in commercially available tubing and rod stock.

A 3 Ml/Hr flow rate, providing a refill time of 10 minutes, may also utilize the 0.0115 inch OD rod 85 in a 36 inch long 0.014 inch space ID tube 83, and a rod length of approximately 21 inches has been found applicable in such instance, the exact length again being determined empirically on an individual test and length adjustment basis at the time of manufacture of the flow control tube assembly 81.

A 2 ML/Hr flow rate or 15 minute refill time has also employed a 0.014 ID tube 83, 36 inches long, and with a 0.012 OD rod 85 which has been found to be approximately 24 inches long, as determined by empirical testing in manufacturer.

In production of the flow control metering tube and rod assemblies 81, the rod 85 length is adjusted until the correct flow is achieved as determined with flow measurement apparatus. The normally encountered tolerances of the rod 85 and tube 83 will cause considerable variation in the rod length of up to approximately ±35%.

In this typical illustrative embodiment the reservoir piston 95 has a diameter of 1.5 inches and an area of 1.767 square inches. The friction force to move the piston 95 has been measured at a piston 95 movement rate of 1 inch per minute and found to vary between 299 grams and 149 grams. The pressure effect has then been calculated to be between 0.189 PSI and 0.374 PSI, with an average of 0.275 PSI. A second test method measured the pressure required to start the piston 95, or the pressure to overcome the static friction condition. This was measured at between 0.7 and 0.8 PSI. By estimating the average pressure loss to be halfway between the static average of 0.75 PSI and the moving average of 0.275 PSI, the average pressure loss caused by piston 95 has been estimated to be approximately 0.51 PSI.

When an actual PCA infusor arrangement 11 has been tested at Denver, Colo., U.S.A., at an ambient atmospheric pressure of 12.12 PSI Absolute, and with the flow rate also tested with a controlled direct air pressure of 9.9 PSI gage pressure, essentially the same effective refill flow rate has been achieved through the flow control tube assembly 81. The difference between the two pressures is 2.2 PSI. Measurement of the dose chamber 23 absolute pressure has revealed such to be 1.3 to 2.0 PSI, which averages out to 1.65 PSI. The friction of the piston 95 in the reservoir syringe barrel 93, is believed to account for the difference, viz. approximately 0.55 PSI.

While the invention has been illustrated and described with respect to a particular illustrative and preferred embodiment end mode of practice, it will be apparent to those skilled in the act that various other embodiments, modifications and improvements may be made without departing from the scope and spirit of the invention. Accordingly, it is to be understood that the invention is not to be limited by the particular illustrative embodiment, but only by the scope of the following appended Claims.

I claim:

1. Patient controllable fluid infusion apparatus comprising a fluid flow metering tube connecting set for attachment between a fluid source under pressure and a use site, which fluid flow metering tube connecting set comprises a flexible metering connecting tube having connector means at its opposite inlet and outlet ends, said connecting and metering tube having a central bore which forms a first fluid flow impedance as a function of the cross-sectional size of said bore, a flow restricting rod having a flow-blocking cross sectional construction with an outer cross sectional size smaller than the cross sectional size of said bore, said rod being disposed within and extending along a selected longitudinal extent of said bore, to thereby form an effective fluid flow passageway bore cross section of reduced cross-sectional size around the outside of and along the longitudinal extent of said rod within said tube bore, which longitudinal extent of reduced cross-sectional size forms a second fluid flow impedance as a function of the longitudinal extent and cross-sectional size of said reduced cross-sectional size effective fluid flow passage way bore along the length of said rod within said bore, a fluid delivery syringe having a fillable fluid chamber from which fluid may be expelled by patient action, a fluid supply reservoir for enabling filling of said chamber, said fluid supply reservoir being connected to said inlet end of said metering connecting tube, and said outlet end of said metering connecting tube being connected in fluid supply relation to said syringe chamber, said fluid delivery syringe having a fluid outlet therefrom for patient controlled dispensing of fluid from its said chamber to a selected site after flow of fluid from said fluid source through said metering connecting tube and around said flow restricting rod as a function of and while maintaining a substantially constant pressure differential between said fluid source and said chamber.

2. Patient controllable fluid infusion apparatus according to claim 1, further comprising a flexible outlet tube in fluid outflow connection with said fluid outlet, and means connected to the outlet end of said outlet tube for fluid flow connection of said outlet tube in fluid flow relation to a patient infusion site.

3. Patient controllable fluid infusion apparatus according to claim 1, in which fluid flow is enabled into said syringe chamber from said fluid source in response to suction within said syringe chamber and further comprising unidirectional valve means enabling unidirectional outflow from said syringe chamber while effectively preventing reverse flow from said selected site back to said chamber.

4. Patient controllable fluid infusion apparatus according to claim 1, said syringe comprising a barrel having a patient controlled piston slidably disposed within said barrel and forming the movable rear end of said chamber, and spring means effective to move said piston rearwardly to quickly enlarge said chamber and thereby create a vacuum within said chamber which enables metered fluid flow at a rate which is a function of the differential pressure between said fluid source and said syringe chamber and the fluid flow impedance of said rod-restricted flexible metering connecting tube.

5. Patient controllable fluid infusion apparatus according to claim 2, the pressure of said fluid source being substantially ambient atmospheric pressure.

6. Patient controllable fluid infusion apparatus according to claim 2, the pressure of said fluid source being greater than ambient atmospheric pressure.

7. Patient controllable fluid infusion apparatus according to claim 1, further comprising visual indicator means for indicating the fluid content status of said fluid source.

8. Patient controllable fluid infusion apparatus according to claim 1, said reservoir comprising a movable container wall onto which ambient atmospheric pressure is applied.

9. Patient controllable fluid infusion apparatus according to claim 1, said fluid reservoir comprising a syringe having a barrel within which said reservoir is formed, and a fluid sealing piston slidable within said barrel and forming a movable wall of said reservoir as a function of the pressure differential on opposite outer and inner faces of said piston.

10. Patient controllable fluid infusion apparatus comprising a fluid flow metering tube connecting set for attachment between a fluid source under pressure and a use site, which flow metering tube connecting set comprises a flexible metering connecting and tube having connector means at its opposite inlet and outlet ends, said metering connecting and tube having a central bore which forms a first fluid flow impedance as a function of the cross-sectional size of said bore, a flow restricting rod having a fluid flow blocking cross sectional construction and an outer cross sectional size smaller than the cross sectional size of said bore, said rod being disposed within and extending along a selected length of said bore, to thereby form an effective fluid flow passageway bore cross section of reduced cross-sectional size along the longitudinal extent of said rod length within said bore, which longitudinal extent of cross-sectional size forms a second fluid flow impedance as a function of the longitudinal extent and cross-sectional size of said reduced effective fluid flow passageway bore along the length of said rod within said bore, a fluid delivery pump having fillable fluid chamber from which fluid may be expelled by patient action, a fluid supply reservoir for enabling filling of said chamber, said fluid supply reservoir being connected to said inlet end of said metering connecting tube, and said outlet end of said metering connecting tube being connected in fluid supply relation to said syringe chamber, said fluid delivery pump having fluid outlet therefrom for patient controlled dispensing of fluid from its said chamber to a selected site after flow of fluid from said fluid source through said metering connecting tube as a function of and while maintaining a substantially constant pressure differential between said fluid source and said chamber.

11. Patient controllable fluid infusion apparatus according to claim 10, further comprising a flexible outlet tube in fluid outflow connection with said fluid outlet, and means connected to the outlet end of said outlet tube for fluid flow connection of said outlet tube in fluid flow relation to a patient infusion site.

12. Patient controllable fluid infusion apparatus according to claim 10, in which metered restricted fluid flow is enabled into said syringe chamber from said fluid source in response to suction within said syringe chamber, and further comprising check valve means enabling unidirectional fluid outflow from said syringe chamber while effectively preventing reverse flow from said selected site back to said chamber.

13. Patient controllable fluid infusion apparatus according to claim 10, said syringe comprising a barrel having a patient controlled piston slidably disposed within said barrel and forming the movable rear end of said chamber, and spring means effective to move said piston rearwardly to quickly enlarge said chamber and thereby create a vacuum within said chamber which enables metered fluid flow at a rate which is a function of the differential pressure between said fluid source and said syringe chamber and the fluid flow impedance of the rod-restricted said flexible metering connecting tube.

14. Patient controllable fluid infusion apparatus according to claim 12, the pressure of said fluid source being substantially ambient atmospheric pressure.

15. Patient controllable fluid infusion apparatus according to claim 12, the pressure of said fluid source being greater than ambient atmospheric pressure.

16. Patient controllable fluid infusion apparatus according to claim 10, said reservoir comprising a movable container wall.

17. Patient controllable fluid infusion apparatus according to claim 10, said fluid reservoir comprising
a syringe having a barrel within which said reservoir is formed,
and a fluid sealing piston slidable within said barrel and forming a movable wall of said reservoir as a function of pressure differential on opposite outer and inner faces of said piston.

18. Patient controlled infusion apparatus, comprising a syringe having a barrel forming a fluid chamber bounded by a fluid sealing rear piston slidable forwardly by a patient to expel fluid from said chamber, spring means biasing said piston rearwardly, fluid inlet and outlet means enabling filling of said chamber with fluid and expelling of fluid from said chamber, fluid reservoir means maintained at a substantially constant pressure and connectable in fluid supply relation with said fluid inlet means for supply of fluid to said chamber, a flexible fluid flow metering tube connected in restricted fluid flow relation between said fluid reservoir and said fluid inlet means, said fluid flow metering tube having a fluid flow bore and a flow-restricting rod having a flow-blocking cross-sectional construction and disposed within said bore and having a selected length, said rod being smaller in cross section than the corresponding cross section of said bore along said selected length, to thereby form a rod-restricted effective fluid flow passageway of lesser cross-sectional area than said bore alone along said rod extending within said bore, which lesser cross-sectional area passageway forms a second greater fluid flow impedance as compared to the fluid flow impedance of said bore without said rod therein, for enabling desired metering of fluid passing between said reservoir and said syringe chamber in response to rearward return movement of said piston by said spring after forward manual movement thereof, and as a function of the length and cross-sectional area of said lesser cross-sectional area fluid passageway, means for connection of said syringe fluid outlet means to a patient fluid infusion site for patient controlled expulsion and application of fluid medication to said infusion site through manual forward movement of said piston against the action of said spring, and check valve means connected in fluid flow relation with said fluid outlet means permitting outflow of fluid from said fluid chamber and preventing return of expelled fluid through said fluid outlet means to said chamber.

19. Patient controlled infusion apparatus according to claim 18, said flow-restricting rod being flexible for flexing as a function of flexing of said flexible fluid flow metering tube in the zone of said rod extent therewithin.

20. Patient controlled infusion apparatus according to claim 18, further comprising means for restraining longitudinal movement of said rod within said bore due to forward fluid flow through said bore and past said rod.

21. Patient controlled infusion apparatus according to claim 18, said selected length of said flow restricting rod within said bore being of an extent relative to the diameter of said rod such that said rod is effectively self-restrained against longitudinal movement within said bore.

22. Patient controlled infusion apparatus according to claim 21,
said rod being of a length at least approximately 300 times the diameter of said rod.

23. Patient controlled infusion apparatus according to claim 18,
said rod being anchored within said bore.

24. Patient controlled infusion apparatus according to claim 18,
said rod being anchored within said bore at one end of said rod.

25. Patient controlled infusion apparatus according to claim 18,
said rod having a wider and thinner securing segment formed thereon, which segment is in securing engagement with the bore wall of said tube.

26. Patient controlled infusion apparatus according to claim 18,
said rod having a deformed end segment which has a cross section engagable in retentive relation at two spaced positions with the bore wall of said tube, while being spaced from said bore wall between said spaced positions.

27. Patient controlled infusion apparatus according to claim 26
said deformed end segment being wider than the inner diameter of said tube bore and thinner than the undeformed cross-sectional size of said rod.

28. The method of controlled intermittent infusion of fluid to a patient infusion site, comprising
metering control of fluid flow from a fluid source to a pump having a fillable fluid dose storage chamber and which is patient-actuatable to pump fluid medication from said fluid storage chamber to a patient infusion site, said metering control comprising
passing fluid from a substantially constant pressure fluid source through a flexible tubular passageway to said fillable fluid dose storage chamber while maintaining a substantially constant pressure differential between said fluid source and said fillable fluid dose storage chamber,
and selectively restricting fluid flow through said tubular passageway by disposing a flow-restricting rod having a flow-blocking cross-section therewithin along a selected longitudinal extent of said passageway, which rod is smaller in cross sectional area than the longitudinally corresponding said tubular passageway along said selected length of said rod,
selectively intermittently actuating said pump to expel fluid from said chamber,
and administering said expelled fluid to a patient infusion site.

29. The method according to claim 1,
in which said rod and said fluid passageway are of effectively substantially constant cross-sectional size along said selected length of said fluid passageway.

30. The method according to claim 1,
wherein said pump has a piston forming a movable wall of said fluid storage chamber and being forwardly movable by patient action to expel fluid from said chamber,
and resiliently biasing said piston rearwardly with a force sufficient to create a vacuum within said chamber for effecting fluid flow from said source and through said flexible fluid passageway having said rod therein and into said fillable fluid storage chamber, which resilient biasing force is sufficiently small to enable ease of patient actuation of said piston for expelling of fluid after fluid charging of said chamber from said source in response to rearward chamber-vacuum-creating movement of said piston.

31. The method according to claim 1,
and selecting said rod extent extending within said tubular passageway to be a length relative to said tubular passageway diameter such that said rod is effectively self-restrained against movement by the flow of fluid therepast.

32. The method according to claim 1,
said maintaining of substantially constant pressure differential comprising the step of effecting substantially constant vacuum within said fluid dose storage chamber, while maintaining a substantially constant positive absolute pressure on fluid medication within said fluid source.

33. The method according to claim 32,
in which said substantially constant positive absolute pressure on fluid medication within said fluid source is effected by subjecting said fluid medication to ambient atmospheric pressure.

34. The method according to claim 1,
said rod being maintained along said selected longitudinal extent of said passageway by securing a fixed length said rod within said passageway.

35. The method according to claim 34,
in which said rod is maintained along said selected longitudinal extent of said passageway by securing one end of said rod within said passageway.

* * * * *